United States Patent [19]

Maul et al.

[11] Patent Number: 4,590,315
[45] Date of Patent: May 20, 1986

[54] PROCESS FOR THE PREPARATION OF HALO AROMATIC COMPOUNDS

[75] Inventors: James J. Maul, Grand Island; David Y. Tang, Amherst, both of N.Y.

[73] Assignee: Occidental Chemical Corporation, Niagara Falls, N.Y.

[21] Appl. No.: 660,765

[22] Filed: Oct. 15, 1984

[51] Int. Cl.$^4$ .................... C07C 17/20; C07C 17/22
[52] U.S. Cl. .................... 570/127; 558/425
[58] Field of Search .................... 260/465 G; 570/127

[56] References Cited

U.S. PATENT DOCUMENTS 4,388,472  6/1983  Cartwright et al. .................... 560/21

Primary Examiner—Dolph H. Torrence
Attorney, Agent, or Firm—James F. Tao; Arthur S. Cookfair; William G. Gosz

[57] ABSTRACT

A process for the preparation of chloro-difluorobenzene compounds of the formula

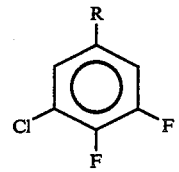

where R is CN or $CF_3$, comprises the steps of (A) reacting an alkali metal fluoride with 4-chloro-3,5-dinitrobenzonitrile or 4-chloro-3,5-dinitrobenzotrifluoride to form the corresponding 4-fluoro-3,5-dinitrobenzonitrile or 4-fluoro-3,5-dinitrobenzotrifluoride product.

(B) chlorodenitrating the 4-fluoro product of step (A) to form the corresponding 3,5-dichloro-4-fluorobenzonitrile or 3,5-dichloro-4-fluorobenzotrifluoride compound.

(C) reacting the 3,5-dichloro-4-fluorobenzonitrile or 3,5-dichloro-4-fluorobenzotrifluoride compound prepared in step (B) with an alkali metal fluoride to form the corresponding 3-chloro-4,5-difluorobenzonitrile or 3-chloro-4,5-difluorobenzotrifluoride compound.

14 Claims, No Drawings

PROCESS FOR THE PREPARATION OF HALO AROMATIC COMPOUNDS

BACKGROUND OF THE INVENTION

This invention relates to a method for the preparation of 3-chloro-4,5-difluorobenzonitrile or 3-chloro-4,5-difluorobenzotrifluoride. The compounds prepared in accordance with the invention are useful as intermediates in the preparation of various chemical products, in particular, in the preparation of substituted diphenyl ethers having herbicidal properties.

A prior art method for preparation of the compound, 3-chloro-4,5-difluorobenzotrifluoride and the use thereof as an intermediate in the manufacture of herbicidal diphenyl ethers is disclosed in U.S. Pat. No. 4,388,472. The preparation disclosed therein involves the steps of (1) reacting chlorine with p-trifluoromethylaniline in glacial acetic acid to form 2,6-dichloro-4-trifluoromethylaniline; (2) diazotization of the latter; (3) reaction of the diazo product with cuprous chloride in concentrated hydrochloric acid to form 3,4,5-trichlorobenzotrifluoride and (4) reaction with KF to form 3-chloro-4,5-difluorobenzotrifluoride. The patent further discloses the preparation of 3,5-dichloro-4-fluorobenzotrifluoride by diazotization of 2,6-dichloro-4-trifluoromethylaniline followed by reaction with sodium fluoroborate and decomposition of the product. Such methods, although useful for laboratory preparations are less suitable for commercial scale preparations. The starting material, p-trifluoromethylaniline, is expensive. Furthermore, the diazotization reaction is expensive and not readily adaptable to commercial scale. Furthermore, step 4 of the prior art route of synthesis, that is, the reaction of KF with 3,4,5-trichlorobenzotrifluoride, leads to the formation of an isomeric mixture of 3-chloro-4,5-difluorobenzotrifluoride and 4-chloro-3,5-difluorobenzotrifluoride, and thus requires additional separation procedures. For similar considerations, the prior art synthetic route utilizing diazotization and halogenation in a manner similar to that detailed above for the preparation of 3-chloro4,5-difluorobenzotrifluoride would also be unsatisfactory, if applied to the analogous commercial scale preparation of 3-chloro-4,5-difluorobenzonitrile.

The compounds prepared in accordance with this invention, that is 3-chloro-4,5-difluorobenzotrifluoride and 3-chloro-4,5-difluorobenzonitrile are useful intermediates for the preparation of herbicidal diphenyl ethers, for example, of the type disclosed in European Patent Application Publication No. 0 23 392, and U.S. Pat. No. 4,388,472.

Accordingly, it is an object of this invention to provide a synthetic route for the preparation of high purity, substantially isomer-free 3-chloro-4,5-difluorobenzonitrile or 3-chloro-4,5-difluorobenzotrifluoride that is well suited for both laboratory and commercial scale preparations. It is a further object to provide a method for the preparation of novel benzonitrile compounds.

SUMMARY OF THE INVENTION

It has now been found that substituted chlorodifluorobenzene compounds of the formula

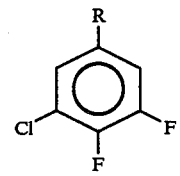

where R is $CF_3$ or CN may be prepared by a process comprising the steps of (A) reacting an alkali metal fluoride with 4-chloro-3,5-dinitrobenzonitrile or 4-chloro-3,5-dinitrobenzotrifluoride to form the corresponding 4-fluoro-3,5-dinitrobenzonitrile or 4-fluoro-3,5-dinitrobenzotrifluoride product.

(B) chlorodenitrating the 4-fluoro product of step (A) to form the corresponding 3,5-dichloro-4-fluorobenzonitrile or 3,5-dichloro-4-fluorobenzotrifluoride compound.

(C) reacting the 3,5-dichloro-4-fluorobenzonitrile or 3,5-dichloro-4-fluorobenzotrifluoride compound prepared in step (B) with an alkali metal fluoride to form the corresponding 3-chloro-4,5-difluorobenzonitrile or 3-chloro-4,5-difluorobenzotrifluoride compound.

The sequence of steps that constitute the process of this invention may be illustrated by the following chemical equation

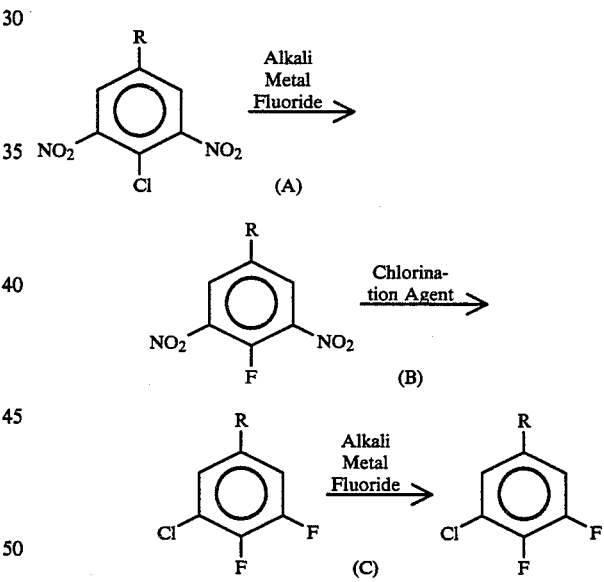

wherein R is CN or $CF_3$.

In the stepwise process detailed above, fluorination steps (A) and (C) are preferably carried out in the liquid phase. The preferred alkali metal fluoride to be employed as a fluorinating agent is potassium fluoride. Either or both of the fluorination steps (A) and (C) may be carried out neat or in the presence of a solvent. It is preferred to carry out step (A) neat and step (C) in the presence of a solvent. Suitable solvents that may be employed in either step (A) or step (C) include, for example, N-methyl-2-pyrrolidone, sulfolane, N,N-dimethylformamide, N,N-dimethylacetamide, N,N-diethylformamide, dimethylsulfoxide, diethylsulfoxide, dipropylsulfoxide, dioctylsulfoxide, dimethylsulfone, diethylsulfone, diphenylsulfone, and the like, and mixtures thereof.

The fluorination reactions are typically carried out at a temperature of from about 50° to about 300° Celsius under atmospheric or superatmospheric conditions. It is preferred to carry out step (A) at a temperature in the range of about 75° to about 155° Celsius. Step (C) is preferably carried out at a temperature of about 170° to about 270° Celsius. When the fluorination is carried out at atmospheric pressure, the selection of a solvent may depend, in part, on the temperature to be employed. Thus, for example, since it is preferred to carry out step (C) at a higher temperature, such as about 200° to about 270° Celsius, a higher boiling solvent such as sulfolane may be selected while a lower boiling solvent such as N,N-dimethylformamide may be appropriate for step (A).

It is preferred to carry out the fluorination steps using a stoichiometric excess of alkali metal fluoride, preferably in a molar ratio of between about 1:1 to about 5:1 of alkali metal fluoride: organic reactant.

The fluorination reactions of steps (A) and (C) proceed readily without the aid of a catalyst. However, a catalyst may be employed effectively to accelerate the reaction. Preferred catalysts are phase transfer catalysts such as tetraphenylphosphonium chloride, hexadecyltributylphosphonium bromide, tetramethylphosphonium chloride, tetramethylammonium chloride, tetradecyltrimethylammonium bromide and the like.

The chlorodenitration step (B) may be carried out in either the vapor phase or the liquid phase and over a wide range of temperatures, for example, from about 50° to abut 500° Celsius. In the liquid phase, the reaction may be carried out neat or in the presence of a solvent. Generally, the liquid phase reaction will be carried out at a temperature of from about 120° to about 250° Celsius under atmospheric pressure. Higher temperatures may be employed under autogenous pressure. Preferably, the chlorodenitration reaction of step (B) is carried out under vapor phase conditions at a temperature of about 250° to about 450° and most preferably about 290° to about 410° Celsius. Various chlorinating agents, such as, $PCl_5$, $SOCl_2$, $HCl$, $Cl_2$ and the like may be employed, the preferred being $Cl_2$.

In another aspect, this invention relates to the preparation of novel benzonitrile compounds. In particular, when 4-chloro-3,5-dinitrobenzonitrile is employed as the starting reactant in the process set forth above, the following novel compounds are prepared: 4-fluoro-3,5-dinitrobenzonitrile, the product of step (A), above; 3,5-dichloro-4-fluorobenzonitrile, the product of step (B), above; and 3-chloro-4,5-difluorobenzonitrile, the product of step (C), above. These halo-substituted benzonitriles are useful intermediates for the preparation of various chemical products, especially herbicidal diphenyl ethers.

The following specific examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE 1—PREPARATION OF 3-CHLORO-4,5-DIFLUOROBENZOTRIFLUORIDE

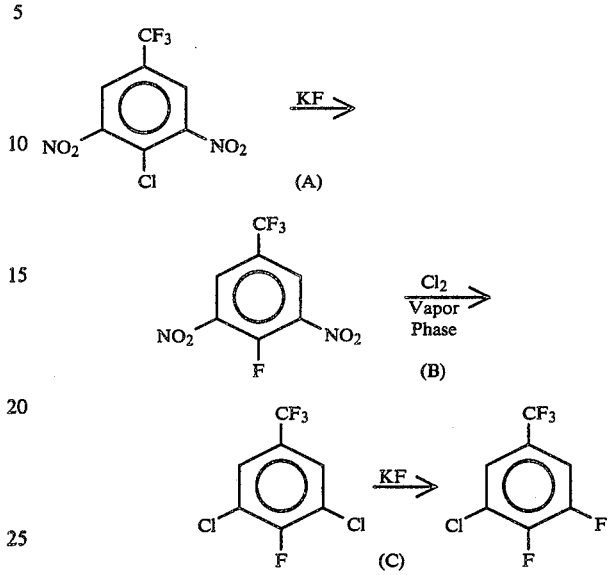

(A) Preparation of 4-fluoro-3,5-dinitrobenzotrifluoride.

A mixture of 7.0 parts of anhydrous potassium fluoride and 5.4 parts of 4-chloro-3,5-dinitrobenzotrifluoride was heated and maintained at about 145° C., with stirring, for 8 hours. The reaction mixture was then extracted with methylene chloride and the extract concentrated to yield 4.32 parts of a brown crystalline solid (m.p. 40°–42.5° C.). Analysis of the product by gas chromatography/mass spectrometry indicated it to be essentially pure 4-fluoro-3,5-dinitrobenzotrifluoride.

(B) Preparation of 3,5-dichloro-4-fluorobenzotrifluoride.

Over a 9.5 hour period a solution of 260 parts of 4-fluoro-3,5-dinitrobenzotrifluorde (prepared as in step A, above) in 1510 parts of carbon tetrachloride was vaporized by passing the solution through a tubular nickel reactor maintained at about 320° C. and the vapors passed through a second tubular nickel reactor, maintained at about 350° C., and mixed therein with a stream of chlorine at a molar ratio of $Cl_2$:4-fluoro-3,5-dinitrobenzotrifluoride of about 6.0. The exiting vapors were condensed to form a yellow solution. The solution was treated with $MgSO_4$ and concentrated. The desired product, 3,5-dichloro-4-fluorobenzotrifluoride, was isolated by vacuum distillation (b.p. 81° C./40 Torr). Analysis of the product using chromatographic techniques indicated a 79.6 percent yield of the desired product at greater than 99 percent purity.

(C) Preparation of 3-chloro-4,5-difluorobenzotrifluoride.

A mixture of 55 parts of anhydrous potassium fluoride and 45.32 parts of 3,5-dichloro-4-fluorobenzotrifluoride in 291 parts of sulfolane was heated and maintained at about 216° to 256° for a period of about 55 hours, while product vapors were removed through a distillation column at a head temperature of about 130°–150° C. A total of 32.02 parts of distillate was collected and analyzed by gas chromatography/mass spectrometry. The distillate was found to be 25.1 percent 3,5-dichloro-4-fluorobenzotrifluoride; 65.9 percent 3-chloro-4,5-difluorobenzotrifluoride; 8.6 percent 3,4,5-trifluorobenzotrifluoride and trace amounts of 4-chloro-3,5-difluorobenzotrifluoride. The desired 3-chloro-4,5-difluorobenzotrifluoride was isolated by distillation (b.p. 122° C.) to recover it in essentially pure form (greater than 99 percent pure). The 3,5-dichloro-4-fluoro isomer is recycled.

EXAMPLE 2—PREPARATION OF 4-FLUORO-3,5-DINITROBENZOTRIFLUORIDE USING PHASE TRANSFER CATALYST

A mixture of 7.0 parts of anhydrous potassium fluoride, 5.4 parts of 4-chloro-3,5-dinitrobenzotrifluoride and 0.5 parts of tetraphenylphosphonium chloride was heated and maintained at about 145° Celsius, with stirring for one hour. Analysis of the crude reaction product, using gas chromatographic techniques, indicated greater than 99.0 percent conversion to 4-fluoro-3,5dinitrobenzotrifluoride.

EXAMPLE 3—PREPARATION OF 3-CHLORO-4,5-DIFLUOROBENZONITRILE

Following the general procedure of Example 1, except that in place of the substituted benzotrifluoride reactant there is employed an equimolar amount of similarly substituted benzonitrile, the compound 3-chloro-4,5-difluorobenzonitrile is prepared in the following manner:

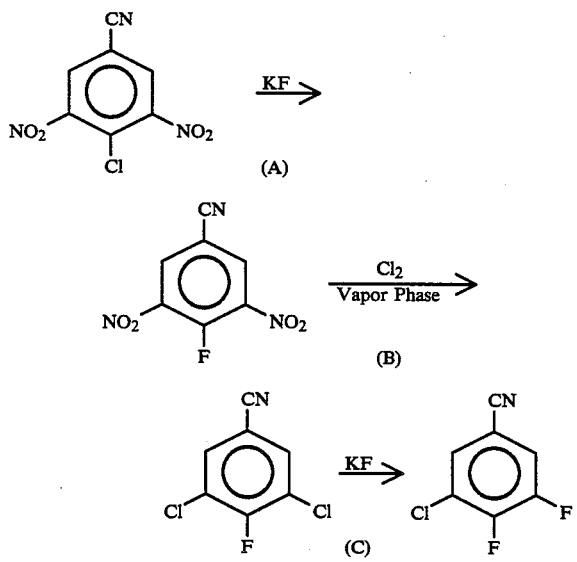

(A) Preparation of 4-fluoro-3,5-dinitrobenzonitrile.

A mixture of 7.0 parts of anhydrous potassium fluoride and 4.5 parts of 4-chloro-3,5-dinitrobenzonitrile is heated and maintained at about 150° C., with stirring for about 8 hours to effect a chlorine-fluorine exchange with the resultant formation of 4-fluoro-3,5-dinitrobenzonitrile.

(B) Preparation of 3,5-dichloro-4-fluorobenzonitrile.

During a 10 hour period a solution of 216 parts of 4-fluoro-3,5-dinitrobenzonitrile (prepared as in step A, above) in 1500 parts of carbon tetrachloride, is vaporized by passing through a tubular nickel reactor maintained at about 350° C. and the vapors passed through a second nickel tubular reactor, maintained at about 350° C., and mixed therein with a stream of chlorine at a molar ratio of $Cl_2$:4-fluoro-3,5-dinitrobenzonitrile of about 6.0. The exiting vapors are collected, condensed and the condensate treated with $MgSO_4$. The desired product, 3,5-dichloro-4-fluorobenzonitrile is isolated by vacuum distillation.

(C) Preparation of 3-chloro-4,5-difluorobenzonitrile

A mixture of 55 parts of anhydrous potassium fluoride and 37 parts of 3,5-dichloro-4-fluorobenzonitrile in 300 parts of sulfolane is heated and maintained, with stirring, at about 250° C. while product vapors are removed through a distillation column to form a condensate containing the desired product, 3-chloro-4,5-difluorobenzonitrile.

The product 3-chloro-4,5-difluorobenzonitrile, prepared for example as set forth in Example 3, above, is a useful intermediate for the preparation of various end products especially for the preparation of diphenyl ether herbicides. Thus, for example, this compound may be further reacted with the potassium salt of methyl-5-hydroxy-2-nitrobenzoate in a solvent, such as N-methyl-2-pyrrolidone at a temperature of about 120° to 180° Celsius to form methyl-5-(2-chloro-4-cyano-6-fluoro-phenoxy)-2-nitro-benzoate. The ester may be hydrolyzed in a conventional manner to the corresponding carboxylic acid.

What is claimed is:

1. A process for the preparation of 3-chloro-4,5-difluorobenzotrifluoride which comprises the steps of
(A) reacting an alkali metal fluoride with 4-chloro-3,5-dinitrobenzotrifluoride to form 4-fluoro-3,5-dinitrobenzotrifluoride;
(B) chlorodenitrating the 4-fluoro product of step (A) to form 3,5-dichloro-4-fluorobenzotrifluoride; and
(C) reacting the 3,5-dichloro-4-fluorobenzotrifluoride compound prepared in step (B) with an alkali metal fluoride to form 3-chloro-4,5-difluorobenzotrifluoride.

2. A process according to claim 1 wherein the alkali metal fluoride of steps (A) and (C) is potassium fluoride.

3. A process according to claim 1 wherein the reactions of steps (A) and (C) are carried out in the liquid phase.

4. A process according to claim 3 wherein the reactions of steps (A) and (C) are carried out neat.

5. A process according to claim 3 wherein the reactions of steps (A) and (C) are carried out in the presence of a solvent.

6. A process according to claim 3 wherein the reaction of step (A) is carried out in the presence of a solvent and the reaction of step (C) is carried out neat.

7. A process according to claim 3 wherein the reaction of step (A) is carried out neat and the reaction of step (C) is carried out in the presence of a solvent.

8. A process according to claim 7 wherein the chlorodenitration reaction of step (B) is carried out in the vapor phase by reacting $Cl_2$ with 4-fluoro-3,5-dinitrobenzotrifluoride.

9. A process according to claim 1 wherein the chlorodenitration reaction of step (B) is carried out in the vapor phase.

10. A process for the preparation of 3-chloro-4,5-difluorobenzotrifluoride which comprises the steps of
(A) reacting potassium fluoride with 4-chloro-3,5-dinitrobenzotrifluoride in the liquid phase, at a temperature of about 75° to about 160° Celsius to form 4-fluoro-3,5-dinitrobenzotrifluoride; and
(B) reacting the 4-fluoro-3,5-dinitrobenzotrifluoride product of step (A) with chlorine in the vapor phase at a temperature of about 290° to about 410° Celsius to form 3,5-dichloro-4-fluorobenzotrifluoride; and (C) reacting the 3,5-dichloro-4-fluorobenzotrifluoride product of step (B) with potassium fluoride in the liquid phase at a temperature of about 170° to about 270° Celsius to form 3-chloro-4,5-difluorobenzotrifluoride.

11. A process according to claim 10 wherein step (C) is carried out in the presence of a solvent.

12. A process according to claim 11 wherein the solvent is sulfolane.

13. A process according to claim 10 wherein step (A) is carried out in the presence of a phase transfer catalyst.

14. A process according to claim 13 wherein the catalyst is tetraphenylphosphonium chloride.

* * * * *